United States Patent
Aase et al.

(10) Patent No.: US 12,361,548 B2
(45) Date of Patent: Jul. 15, 2025

(54) METHOD AND SYSTEM FOR PROVIDING AN OBJECTIVE IMAGE QUALITY METRIC AFTER ULTRASOUND IMAGE ACQUISITION AND PRIOR TO PERMANENT STORAGE

(71) Applicant: GE Precision Healthcare LLC, Wauwatosa, WI (US)

(72) Inventors: Svein Arne Aase, Trondheim (NO); Kai-Uwe Lempertz, Taunusstein (DE)

(73) Assignee: GE Precision Healthcare LLC, Waukesha, WI (US)

( * ) Notice: Subject to any disclaimer, the term of this patent is extended or adjusted under 35 U.S.C. 154(b) by 150 days.

(21) Appl. No.: 18/086,372

(22) Filed: Dec. 21, 2022

(65) Prior Publication Data

US 2024/0212134 A1     Jun. 27, 2024

(51) Int. Cl.
*G06T 7/00* (2017.01)
*A61B 8/00* (2006.01)
*G06V 10/26* (2022.01)

(52) U.S. Cl.
CPC .......... *G06T 7/0012* (2013.01); *A61B 8/463* (2013.01); *A61B 8/54* (2013.01); *G06V 10/26* (2022.01); *G06T 2207/10132* (2013.01); *G06T 2207/30048* (2013.01); *G06V 2201/031* (2022.01)

(58) Field of Classification Search
CPC ......... G06T 7/0012; G06T 2207/10132; G06T 2207/30048; G06V 10/26; G06V 2201/031; A61B 8/463; A61B 8/54
See application file for complete search history.

(56) References Cited

U.S. PATENT DOCUMENTS

| | | | |
|---|---|---|---|
| 2002/0072670 A1* | 6/2002 | Chenal | A61B 8/485 600/449 |
| 2002/0072671 A1* | 6/2002 | Chenal | G06T 7/12 600/450 |
| 2002/0072672 A1* | 6/2002 | Roundhill | A61B 8/483 600/450 |
| 2002/0072674 A1* | 6/2002 | Criton | A61B 8/485 600/454 |
| 2004/0077952 A1* | 4/2004 | Rafter | A61B 8/463 600/481 |
| 2004/0126007 A1* | 7/2004 | Ziel | G06T 15/08 382/128 |

(Continued)

*Primary Examiner* — Dixomara Vargas
(74) *Attorney, Agent, or Firm* — McAndrews, Held & Malloy, Ltd.; Daniel Bissing; David Bates

(57) ABSTRACT

A system and method for providing an objective image quality metric of an image loop of ultrasound images after acquisition of the image loop and prior to permanently storing the image loop is provided. The method includes performing, by an ultrasound probe of an ultrasound system, an acquisition of an image loop of a plurality of ultrasound images. The method includes stop performing the acquisition by the ultrasound probe of the image loop of the plurality of ultrasound images. The method includes processing, by at least one processor of the ultrasound system after the stop performing the acquisition by the ultrasound probe, the image loop of the plurality of ultrasound images to generate an objective image quality metric. The method includes causing, by the at least one processor, a display system to present a visual representation of the objective image quality metric.

20 Claims, 6 Drawing Sheets

(56) References Cited

U.S. PATENT DOCUMENTS

| | | | |
|---|---|---|---|
| 2007/0016019 A1* | 1/2007 | Salgo | G06T 7/62 600/437 |
| 2021/0030402 A1 | 2/2021 | Aase et al. | |
| 2021/0169455 A1* | 6/2021 | Annangi | A61B 8/54 |
| 2021/0174496 A1* | 6/2021 | Annangi | A61B 8/52 |
| 2021/0192720 A1* | 6/2021 | Annangi | A61B 8/58 |
| 2022/0122256 A1* | 4/2022 | Hartkens | G16H 50/20 |

* cited by examiner

METHOD AND SYSTEM FOR PROVIDING AN OBJECTIVE IMAGE QUALITY METRIC AFTER ULTRASOUND IMAGE ACQUISITION AND PRIOR TO PERMANENT STORAGE

FIELD

Certain embodiments relate to ultrasound imaging. More specifically, certain embodiments relate to a method and system for analyzing and providing an objective image quality metric of an image loop of ultrasound images after acquisition of the image loop and prior to permanently storing the image loop.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

An ultrasound operator typically manually reviews ultrasound images during or immediately after acquisition to determine whether all of the appropriate image views have been acquired. The ultrasound operator may also attempt to manually determine inadequacies of the acquired ultrasound images. However, even experienced ultrasound operators may be unable to definitively, consistently, and accurately determine whether the acquired ultrasound images are suitable for various measurements. Instead, such manual analysis is subjective, inconsistent, and error prone, particularly with image loops having a plurality of recorded image frames. Possible inadequacies with acquired ultrasound images, such as non-standard views, unintended heart rate variability, inconsistent anatomical structure dimensions in acquired images, and the like, may not be definitively, consistently, and accurately detected using the manual review approach. If the acquired images are later determined to be unsuitable, the patient may be asked to return to undergo an additional ultrasound examination, which may be inconvenient, inefficient, and costly.

Real-time scan guidance and quality feedback during live ultrasound imaging is known. However, live feedback during an ultrasound examination may clutter a display, which may be distracting and/or otherwise annoying to an ultrasound operator. Computing resources may also be limited during ultrasound scanning, limiting the ability to provide robust quality analysis and feedback. The permanent (i.e., long term) storage of unsuitable images may also limit memory resources.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for providing an objective image quality metric of an image loop of ultrasound images after acquisition of the image loop and prior to permanently storing the image loop, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
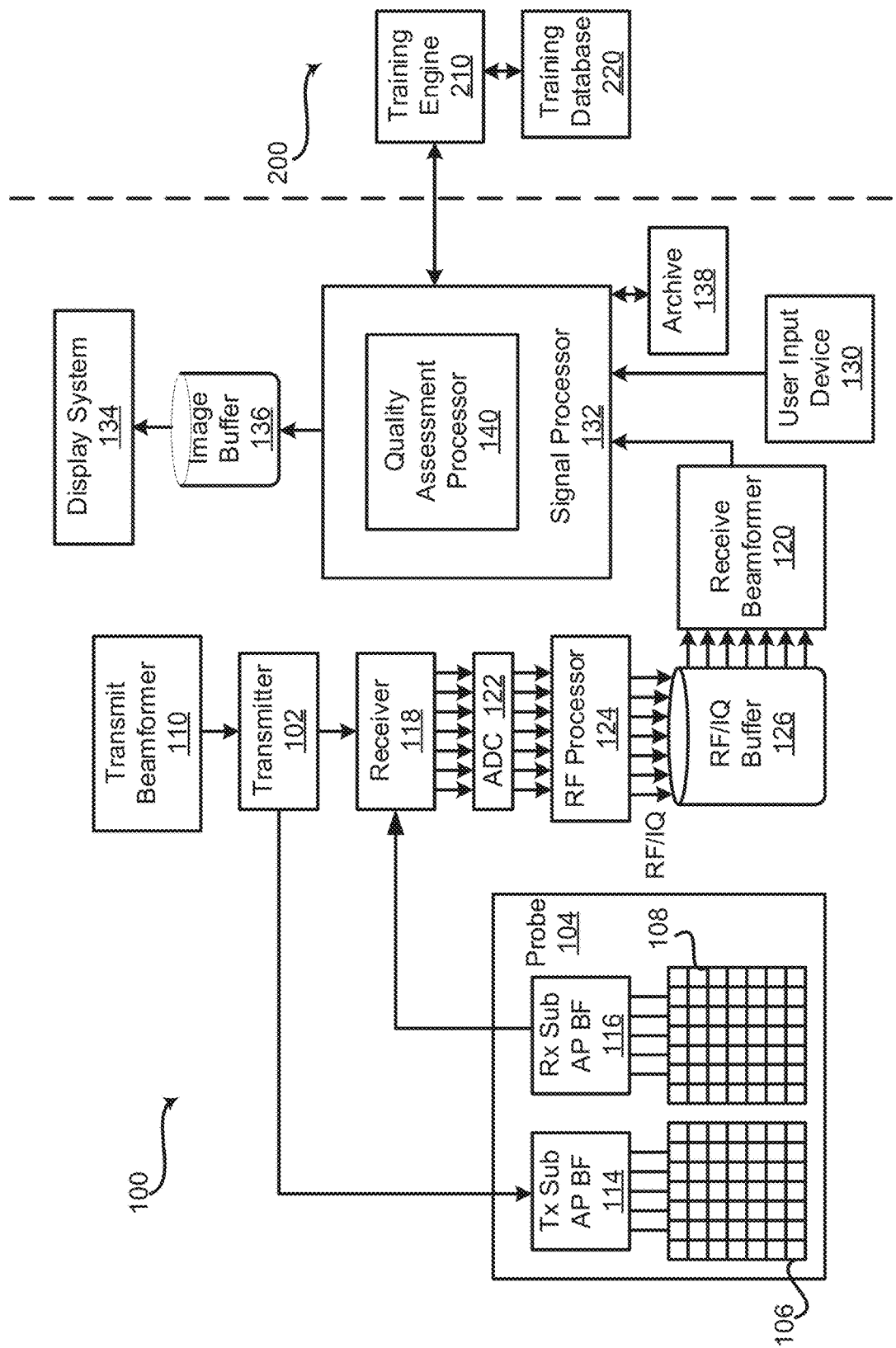
FIG. 1 is a block diagram of an exemplary ultrasound system that is operable to provide an objective image quality metric of an image loop of ultrasound images after acquisition of the image loop and prior to permanently storing the image loop, in accordance with various embodiments.

Certain embodiments may be found in a method and system for providing an objective image quality metric of an image loop of ultrasound images after acquisition of the image loop and prior to permanently storing the image loop. Various embodiments have the technical effect of optimizing computing resources by automatically analyzing an image loop of ultrasound images after ultrasound image acquisition has stopped (i.e., when most computing resources of the ultrasound system are idle). Aspects of the present disclosure have the technical effect of maximizing memory resources by refraining from storing the image loop of ultrasound images in permanent (i.e., long-term) memory until a quality determination is made based on an objective image quality metric. Certain embodiment have the technical effect of maximizing memory resources by discarding unsuitable image loops of ultrasound images prior to storing the image loop of ultrasound images in permanent (i.e., long-term) memory. Various embodiments have the technical effect of providing objective image quality metrics without cluttering a display during ultrasound image acquisition. Aspects of the present disclosure have the technical effect of identifying unsuitable image loops of ultrasound images prior to a patient leaving the ultrasound examination. Certain embodiments have the technical effect of presenting image quality metrics that provide objective, definitive, consistent, accurate, and reliable feedback to an ultrasound operator regarding whether the acquired image loop of ultrasound images are suitable for various measurements. Various embodiments have the technical effect of automatically storing an image loop of ultrasound images if the objective image quality metric is above a threshold.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams. Moreover, as used herein, the term "image" broadly refers to both single images and image loops (e.g., a recording of a plurality of still frames stored together).

Furthermore, the term processor or processing unit, as used herein, refers to any type of processing unit that can carry out the required calculations needed for the various embodiments, such as single or multi-core: CPU, Graphic Processing Unit (GPU), Accelerated Processing Unit (APU), Graphics Board, DSP, FPGA, ASIC or a combination thereof. Moreover, the terms permanently storing and/or long-term storage refer to storing at persistent, non-volatile storage, which maintains data even after being powered off.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to provide an objective image quality metric of an image loop of ultrasound images after acquisition of the image loop and prior to permanently storing the image loop, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, initiate and/or stop ultrasound image acquisition, store and/or discard image loops of ultrasound images, and the like. In an exemplary embodiment, the user input device 130 may be operable to configure, manage and/or control operation of one or more components, processes, and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a quality assessment processor 140. The signal processor 132 may be capable of receiving input information from a user input device 130 and/or archive 138, generating an output displayable by a display system 134, and manipulating the output in response to input information from a user input device 130, among other things. The signal processor 132 and quality assessment processor 140 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a quality assessment processor 140 that comprises suitable logic, circuitry, interfaces and/or code that may be operable to analyze acquired image loops of ultrasound images after image acquisition has stopped to generate an objective image quality metric. The quality assessment processor 140 may include image analysis algorithms, one or more deep neural networks (e.g., a convolutional neural network) and/or may utilize any suitable form of image analysis techniques or machine learning processing functionality configured to automatically generate an objective image quality metric of anatomical structure(s) depicted in the ultrasound image data. For example, the quality assessment processor 140 may include one or more analysis processes or algorithms such as, view recognition, structure recognition, spectrum recognition, end diastole estimation, automated functional imaging (AFI) analysis (e.g., trackability of segments), ejection fraction analysis (e.g., end diastole and end systole contour overlap), artificial intelligence (AI) confidence analysis, sphericity analysis, segmentation, automated measurements (e.g., left ventricle (LV) study, apex movement, cardiac automated Doppler, etc.), heart rate compatibility analysis, automated clinical findings (e.g., diastology assessment), image coherence, image tilt/rotation offset, and the like.

For example, view and spectrum recognition processes or algorithms may be executed by the quality assessment processor 140 to identify potential non-standard views if a view provided by an image is not recognized. The view and spectrum recognition processes or algorithms may be configured to identify unsuitable ultrasound images and/or image loops of ultrasound images, such as to perform automated functional imaging (AFI) analysis, American Society of Echocardiography (ASE) guideline measurements, or the like. As an example, if performing AFI analysis, the view and spectrum recognition processes or algorithms may identify if any of a four-chamber (4CH) view, a two-chamber (2CH) view, or an apical long-axis (APLAX) view is unsuitable.

As another example, automated measurements and automated clinical findings processes or algorithms may be executed by the quality assessment processor 140 to identify images having inadequacies that may prevent subsequent automated measurements or other analysis. For example, the automated measurement processes or algorithms may attempt to execute automated measurements (e.g., an LV study on identified parasternal long-axis (PLAX) images or cardiac automated Doppler on identified spectrum images) and identify images that have a measurement confidence level below a pre-determined threshold.

Additionally, an end diastole estimation process or algorithm may be executed by the quality assessment processor 140 to generate a heart rate graph as a function of time during an ultrasound examination for all of the images in the examination. For example, in regular echo examinations (not stress echo), the goal is to acquire all images at approximately a same heart rate to allow measurements calculated based on multiple images to evaluate the health of the heart at rest. However, a stress level of a patient may vary during the course of the examination due to discomfort, psychology, and/or random events. Additionally, extra systole or other rhythm disturbances could occur without the ultrasound operator noticing the disturbances (e.g., if an operator is recording multiple cycles). Also, problems may arise with an ECG signal quality and/or the QRS trig algorithm. The above exemplary factors may bias the resulting measurements and analysis without an ultrasound operator noticing at or before the end of the ultrasound examination (i.e., when new recordings could have been acquired). Accordingly, the heart rate estimates may be extracted from ECG trig to ECG trig (QR-QR intervals) based on an electrocardiogram (ECG) and plotted against the exam times as provided for each image in the raw data/DICOM header. As another example, the quality assessment processor 140 may be configured to generate a heart rate compatibility metric identifying whether a first heart rate corresponding with an image loop of ultrasound images is within a compatibility threshold with at least one other heart rate corresponding with at least one other image loop permanently stored at an archive 138 of the ultrasound system 100.

Furthermore, a segmentation process or algorithm may be executed by the quality assessment processor 140 to identify dimension problems with imaged structures. For example, an artificial intelligence segmentation process or algorithm may be executed on the acquired ultrasound images. The segmentation process or algorithm may extract lengths and/or diameters, such as a length or diameter of a left ventricle in multiple ultrasound images at end diastole and end systole. The extracted lengths and/or diameters from the plurality of ultrasound images may be compared to identify outliers (e.g., inconsistent measurements). The existence of outliers may indicate probe misplacement during image acquisition with respect to one or more of the ultrasound images.

In addition, automated functional imaging (AFI) analysis processes or algorithms may be executed by the quality assessment processor 140 to identify segments that may not be trackable for strain analysis. The AFI analysis processes or algorithms may identify segments in the ultrasound image data and output trackability results for each of the identified segments.

Moreover, tracking or segmentation processes or algorithms (e.g., ejection fraction tools or left heart chamber volumetric tools) may be executed by the quality assessment processor 140 to identify foreshortening problems. For example, inexperienced operators may have difficulty positioning the ultrasound probe 104 for various examinations, which may result in inconsistent measured anatomical structure dimensions and/or foreshortening. As an example, if an ultrasound operator fails to properly position the ultrasound probe at the apex of the heart when acquiring apical images, the imaged apex of the left ventricle as visible at the display system 134 may be at a different position at end-diastole compared to at end-systole, which would likely indicate foreshortening of the left ventricle. Measurements based on foreshortened images may be inaccurate and/or misleading. As another example, if an ultrasound operator fails to properly position the ultrasound probe at the thickest part of the left ventricle when attempting to acquire a parasternal long axis (PLAX) view, a measured diameter of the left ventricle in the incorrectly acquired ultrasound image may be inaccurate and inconsistent with the diameter estimated in apical view images. Accordingly, the quality assessment processor 140 may execute tracking or segmentation processes providing heart contours, graphs, or points at end diastole and end systole that are compared to determine an amount of movement of an apical point depicted in the image loop of the plurality of ultrasound images over a time period (e.g. a heart cycle).

In various embodiments, any of the analysis processes or algorithms provided as a deep neural network executed by the quality assessment processor 140 may be made up of, for example, an input layer, an output layer, and one or more hidden layers in between the input and output layers. Each of the layers may be made up of a plurality of processing nodes that may be referred to as neurons. For example, an artificial intelligence view recognition analysis process or algorithm may include an input layer having a neuron for each pixel or a group of pixels from a scan plane of an anatomical structure. The output layer may have a neuron corresponding to a plurality of pre-defined views. As an example, if imaging a heart, the output layer may include neurons for a 4CH view, a 2CH view, an APLAX view, a PLAX view, a short-axis apical level (SAX-AP) view, a short-axis papillary muscle level (SAX-PM) view, a short-axis mitral valve level (SAX-MV) view, an unknown view, an other view, and/or any suitable view. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the quality assessment processor 140 view recognition deep neural network (e.g., convolutional neural network) may identify image views of an anatomical structure in ultrasound image data with a high degree of probability.

The quality assessment processor 140 may be configured to generate an objective image quality metric based on the processes and/or algorithms described above, such as view recognition, structure recognition, spectrum recognition, end diastole estimation, automated functional imaging (AFI) analysis (e.g., trackability of segments), ejection fraction analysis (e.g., end diastole and end systole contour overlap), artificial intelligence (AI) confidence analysis, sphericity analysis, segmentation, automated measurements (e.g., left ventricle (LV) study, apex movement, cardiac automated Doppler, etc.), heart rate compatibility analysis, automated clinical findings (e.g., diastology assessment), image coherence, image tilt/rotation offset, and the like. The quality assessment processor 140 is configured to analyze the acquired image loop of ultrasound images immediately after ultrasound image acquisition is complete to maximize computational resources for the robust assessment of the ultrasound images of the image loop. The quality assessment processor 140 causes the display system 134 to present the objective image quality metric in nearly real-time after the ultrasound probe 104 stops acquiring ultrasound images of the image loop. In various embodiments, the objective image quality metric may be presented with a preview of the acquired image loop of ultrasound images.

Figure 2:
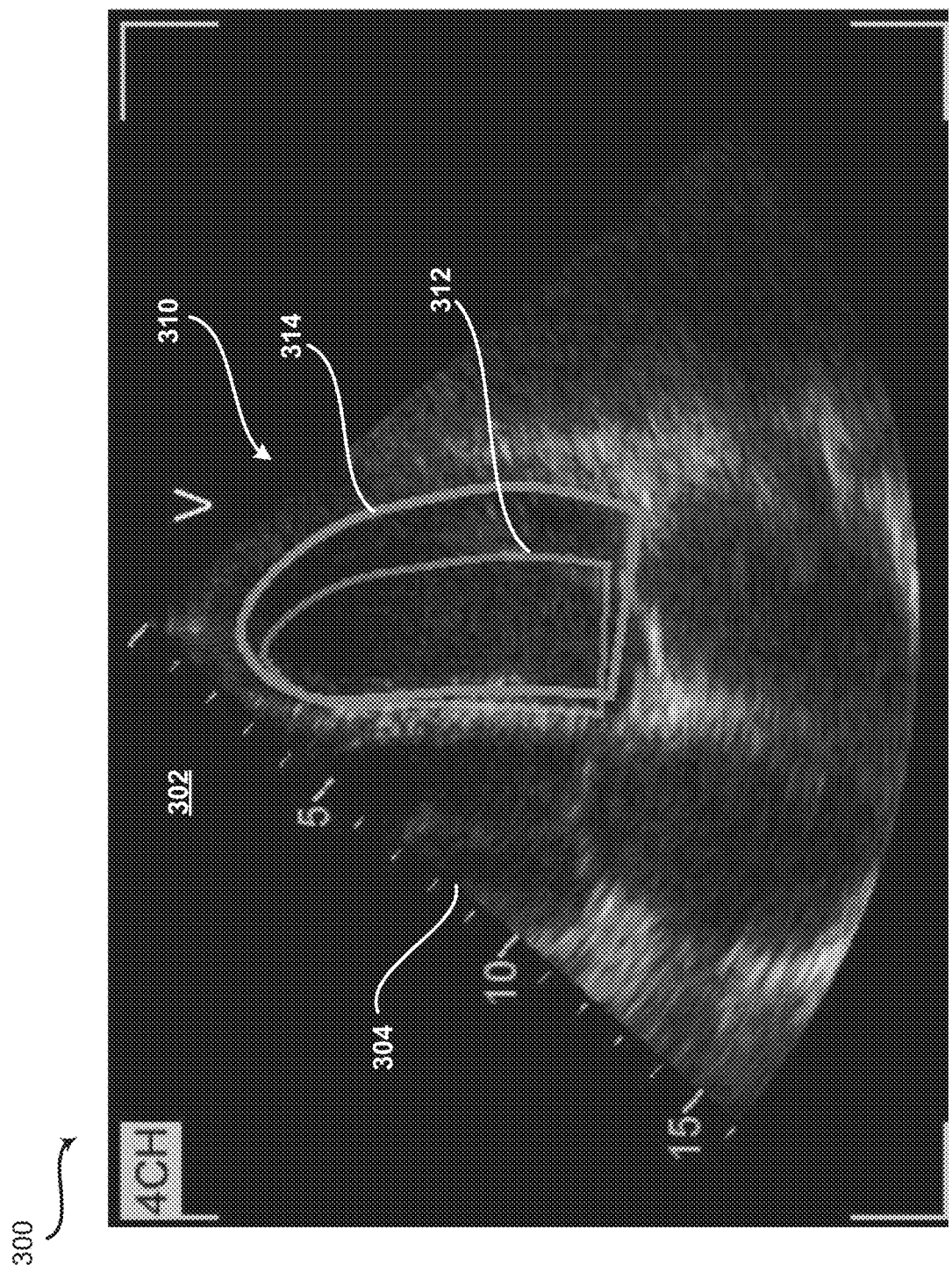
FIG. 2 is a display of an exemplary visual representation of an objective image quality metric graphically identifying foreshortening, in accordance with various embodiments.
Figure 3:
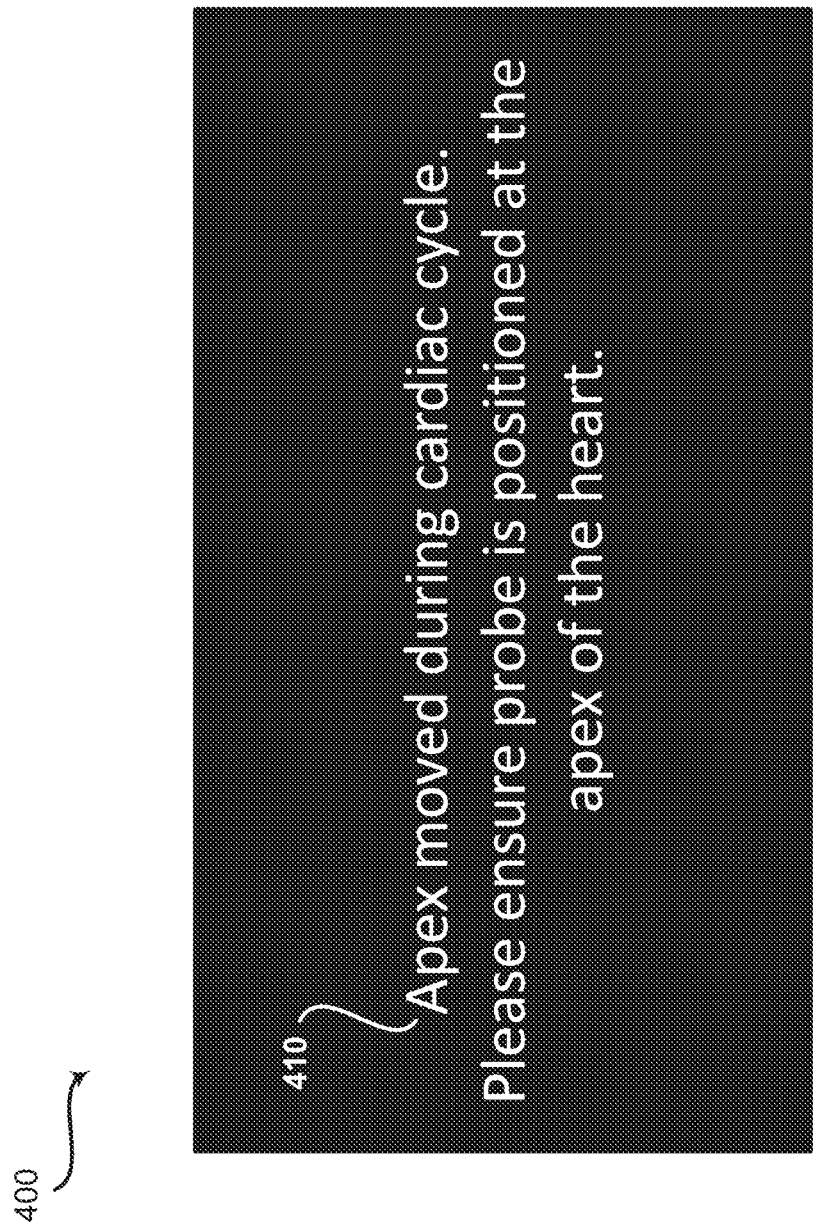
FIG. 3 is a display of an exemplary visual representation of an objective image quality metric textually identifying foreshortening and providing instructions guiding a user to address the foreshortening problem, in accordance with various embodiments.
Figure 4:
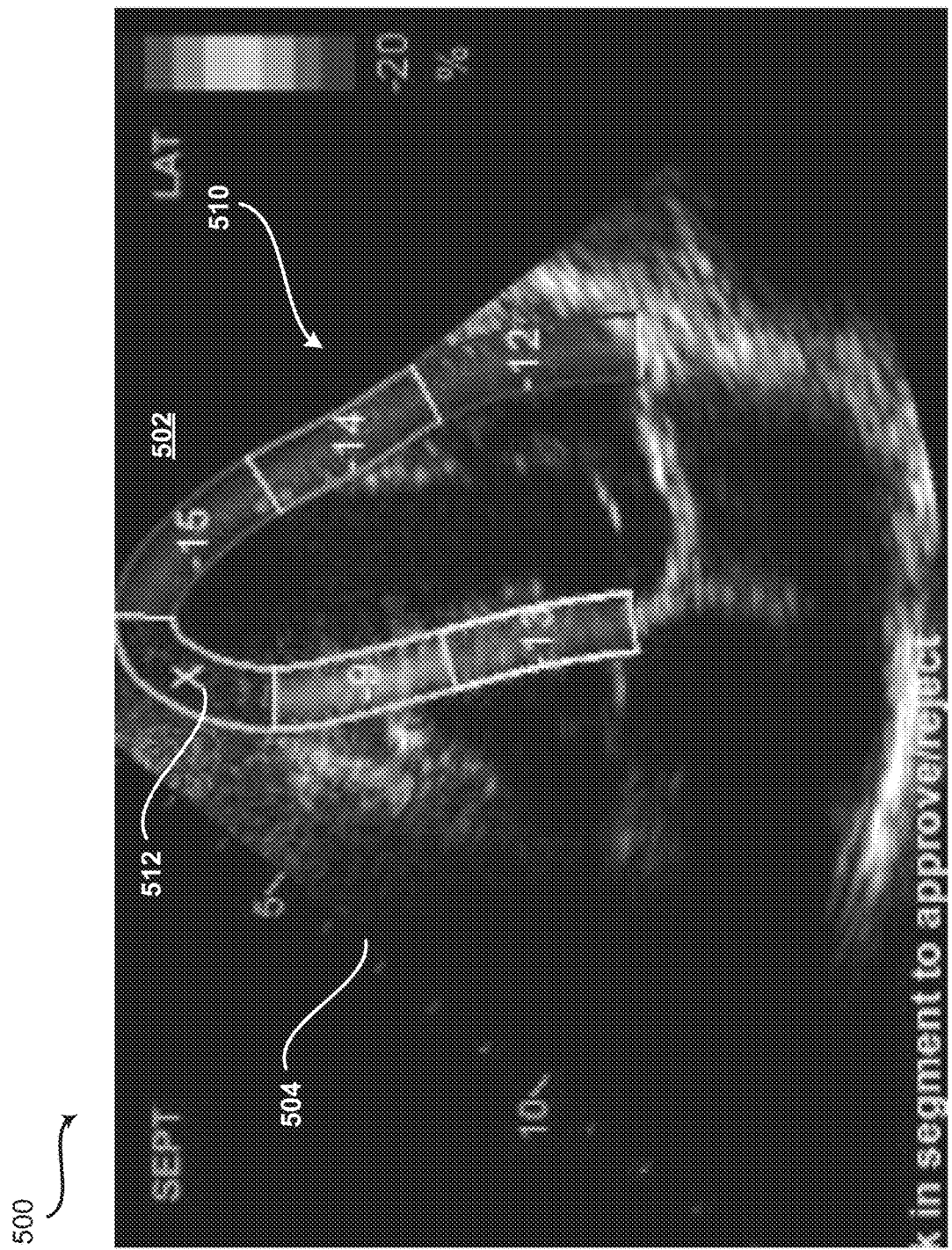
FIG. 4 is a display of an exemplary objective image quality metric graphically identifying a segment unsuitable for tracking in performing strain analysis, in accordance with various embodiments.
Figure 5:
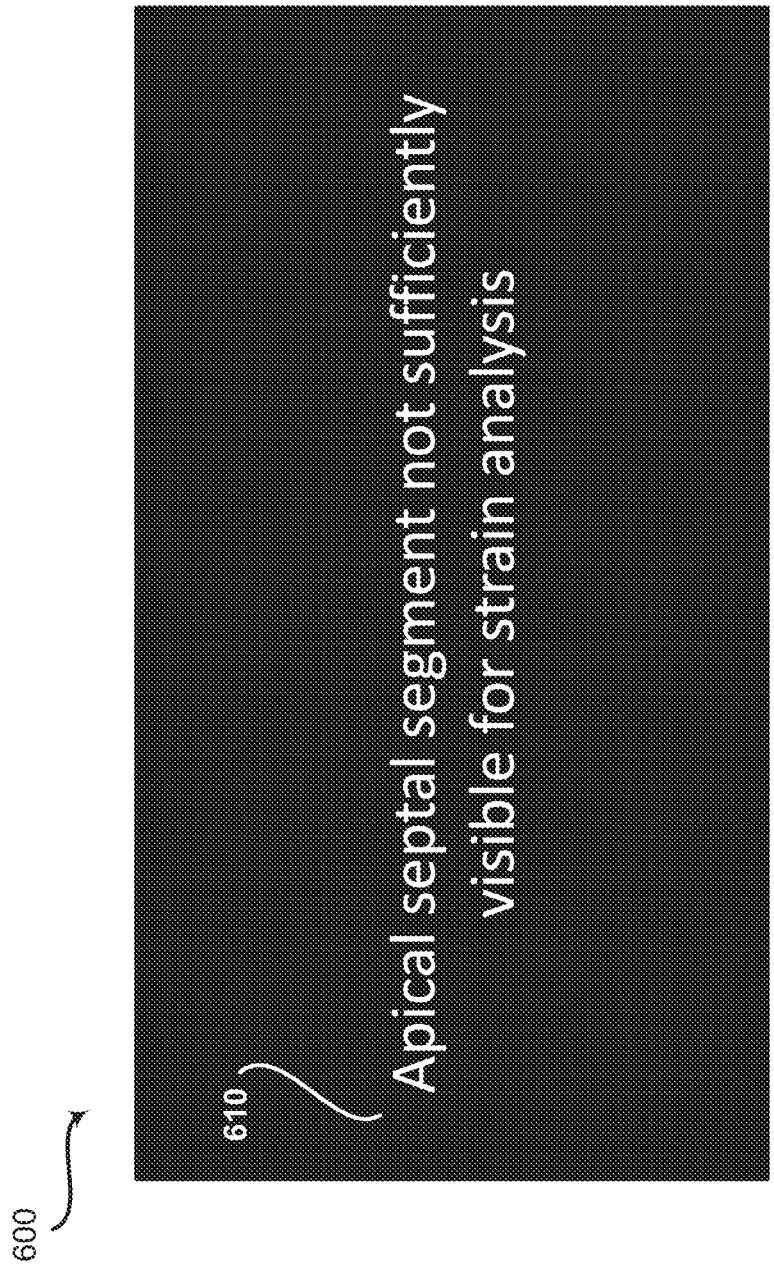
FIG. 5 is a display of an exemplary objective image quality metric textually identifying a segment unsuitable for tracking in performing strain analysis, in accordance with various embodiments.

The objective image quality metric may comprise a graphical representation identifying a problem with the image loop of the plurality of ultrasound images, a textual representation identifying the problem with the image loop of the plurality of ultrasound images, and/or instructions guiding a user to address the problem with the image loop of the plurality of ultrasound images. For example, a graphical representation of the objective image quality metric may be a foreshortening metric identifying an amount of movement of an apical point depicted in the image loop of ultrasound images over a time period as shown in FIG. 2. Additionally and/or alternatively, a textual representation of the foreshortening metric along with instructions for resolving the foreshortening problem may be presented at the display system 134 as shown in FIG. 3. As another example, a graphical representation of the objective image quality metric may be a strain analysis metric identifying a trackability of each of a plurality of segments of a left ventricle depicted in the image loop of ultrasound images, as shown in FIG. 4. Additionally and/or alternatively, a textual representation of the strain analysis metric may be presented at the display system 134 as shown in FIG. 5. The objective image quality metric may further include numerical values, grades, symbols, color-coding, directional indicators, and/or the like for identifying problems in the ultrasound image data and/or providing instructions for addressing identified problems in the ultrasound image data.

FIG. 2 is a display 300 of an exemplary visual representation of an objective image quality metric 310 graphically identifying foreshortening 312, 314, in accordance with various embodiments. Referring to FIG. 2, the display 300 comprises an image display portion 302 comprising an ultrasound image 304 and an exemplary graphical objective image quality metric 310. In the example of FIG. 2, the graphical objective image quality metric 310 is a foreshortening metric identifying an amount of movement of an apical point depicted in the image loop of the plurality of ultrasound images over a time period (e.g., a heart cycle). Specifically, the quality assessment processor 140 of the signal processor 132 may execute landmark detection/segmentation and tracking processes or algorithms (e.g., ejection fraction tools or left heart chamber volumetric tools) to identify foreshortening problems. The graphical objective image quality metric may comprise a heart contour at end systole 312 of a heart cycle and a heart contour at end diastole 314 of the heart cycle. The top portions of the heart contours 312, 314 are offset horizontally and vertically illustrating movement of the apical point corresponding with a foreshortening problem. Accordingly, an ultrasound operator may provide a user input via a user input device 130, such as a freeze button, to discard the image loop of ultrasound images 304 and resume acquisition of an additional image loop of ultrasound images with the ultrasound probe 104 repositioned at the apex of the heart. Alternatively, if the ultrasound operator is satisfied with the image loop of ultrasound images based on the objective image quality metric 310, the ultrasound operator may provide a user input via a user input device 130, such as an image store button, to permanently store the image loop of ultrasound images 304 to archive 138 and/or any suitable long-term data storage medium.

FIG. 3 is a display 400 of an exemplary visual representation of an objective image quality metric 410 textually identifying foreshortening and providing instructions guiding a user to address the foreshortening problem, in accordance with various embodiments. Referring to FIG. 3, the display 400 comprises an exemplary textual objective image quality metric 410. In various embodiments, the textual objective image quality metric 410 may be presented at the display system 134 with a preview of the acquired image loop for review by the ultrasound operator. In the example of FIG. 3, the textual objective image quality metric 410 is a foreshortening metric identifying an amount of movement of an apical point depicted in the image loop of the plurality of ultrasound images over a time period (e.g., a heart cycle). Specifically, the quality assessment processor 140 of the signal processor 132 may execute processes or algorithms to identify foreshortening problems. The quality assessment processor 140 may generate a textual objective image quality metric 410 describing movement of the apical point corresponding with a foreshortening problem. For example, in FIG. 3, the textual objective image quality metric 410 states, "Apex moved during cardiac cycle." In various embodiments, the textual objective image quality metric 410 may further provide instructions for addressing the foreshortening problem. For example, in FIG. 3, the textual objective quality metric 410 states, "Please ensure probe is positioned at the apex of the heart." Accordingly, an ultrasound operator may select a user input device 130, such as a freeze button, to discard the image loop of ultrasound images and resume acquisition of an additional image loop of ultrasound images with the ultrasound probe 104 repositioned at the apex of the heart. Alternatively, if the ultrasound operator is satisfied with the image loop of ultrasound images based on the objective image quality metric 410, the ultrasound operator may select a user input device 130, such as an image store button, to permanently store the image loop of ultrasound images to archive 138 and/or any suitable long-term data storage medium.

FIG. 4 is a display 500 of an exemplary objective image quality metric 510 graphically identifying a segment unsuitable for tracking 512 in performing strain analysis, in accordance with various embodiments. Referring to FIG. 4, the display 500 comprises an image display portion 502 comprising an ultrasound image 504 and an exemplary graphical objective image quality metric 510. In the example of FIG. 4, the graphical objective image quality metric 510 is a strain analysis metric identifying a trackability of each of a plurality of segments of a left ventricle depicted in the image loop of the plurality of ultrasound images 504. The trackability of each of the plurality of segments corresponds with an ability to perform a strain analysis. Specifically, the quality assessment processor 140 of the signal processor 132 may execute automated functional imaging (AFI) analysis processes or algorithms and/or any suitable tracking based regional strain tool to identify segments that may not be trackable for strain analysis. The graphical objective image quality metric 510 may comprise an identification of a plurality of segments of the imaged left ventricle. The graphical objective image quality metric 510 may comprise identifiers 512 of non-trackable segments. The identifiers 512 of the graphical objective image quality metric 510 may include text, symbols, color-coding, or the like for identifying the trackability of the segments. In the example of FIG. 4, the identifier 512 is an "X" provided on the apical septal segment to provide feedback to the ultrasound operator that the apical septal segment is not sufficiently visible (i.e., not trackable) for strain analysis. Accordingly, an ultrasound operator may provide a user input via a user input device 130, such as a freeze button, to discard the image loop of ultrasound images 504 and resume acquisition of an additional image loop of ultrasound images. Alternatively, if the ultrasound operator is satisfied with the image loop of ultrasound images based on the objective image quality metric 510, the ultrasound operator may provide a user input via a user input device 130, such as an image store button, to permanently store the image loop of ultrasound images 504 to archive 138 and/or any suitable long-term data storage medium.

FIG. 5 is a display of an exemplary objective image quality metric 610 textually identifying a segment unsuitable for tracking in performing strain analysis, in accordance with various embodiments. Referring to FIG. 5, the display 600 comprises an exemplary textual objective image quality metric 610. In various embodiments, the textual objective image quality metric 610 may be presented at the display system 134 with a preview of the acquired image loop for review by the ultrasound operator. In the example of FIG. 5, the textual objective image quality metric 610 is a strain analysis metric identifying a trackability of each of a plurality of segments of a left ventricle depicted in the image loop of the plurality of ultrasound images. The trackability of each of the plurality of segments corresponds with an ability to perform a strain analysis. Specifically, the quality assessment processor 140 of the signal processor 132 may execute processes or algorithms to identify segments that may not be trackable for strain analysis. The quality assessment processor 140 may generate a textual objective image quality metric 610 describing the trackability of segments for performing strain analysis. For example, in FIG. 5, the textual objective image quality metric 610 states, "Apical septal segment not sufficiently visible for strain analysis." Accordingly, an ultrasound operator may select a user input device 130, such as a freeze button, to discard the image loop of ultrasound images and resume acquisition of an additional image loop of ultrasound images. Alternatively, if the ultrasound operator is satisfied with the image loop of ultrasound images based on the objective image quality metric 610, the ultrasound operator may select a user input device 130, such as an image store button, to permanently store the image loop of ultrasound images to archive 138 and/or any suitable long-term data storage medium.

Referring again to FIG. 1, the quality assessment processor 140 may be configured to store the image loop of ultrasound images permanently (i.e., long-term storage) or discard the image loop of ultrasound images in response to a received user input via the user input device 130. For example, an ultrasound operator may select an image store button and/or any suitable user input device 130 based on the presented objective image quality metric identifying the image loop of ultrasound images being suitable for subsequent measurements and/or analysis. Additionally and/or alternatively, the ultrasound operator may select a freeze button or any suitable user input device 130 to discard the image loop of ultrasound images and resume acquisition of an additional image loop of ultrasound images based on the presented objective image quality metric identifying the image loop of ultrasound images being unsuitable for subsequent measurements and/or analysis. In an exemplary embodiment, the quality assessment processor 140 may additionally and/or alternatively be configured to automatically store the image loop of ultrasound images permanently (i.e., long-term storage) or discard the image loop of ultrasound images based on comparison of the objective image quality metric to a pre-defined threshold.

In various embodiment, the processes and/or algorithms executed by the quality assessment processor 140 may be based on default settings, user-configurable settings, ultrasound examination type, and/or the like. The visual representation of the objective image quality metric (e.g., graphical, textual, and/or instructional) may be based on default setting, user-configurable settings, or the like.

The display system 134 may be any device capable of communicating visual information to a user. For example, a display system 134 may include a liquid crystal display, a light emitting diode display, and/or any suitable display or displays. The display system 134 can be operable to present image loops of ultrasound images 304, 504, objective image quality metrics 301, 410, 510, 610, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores image loops of ultrasound images 304, 504 and/or instructions for generating and presenting objective image quality metrics 310, 410, 510, 610, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the quality assessment processor 140. For example, the artificial intelligence model inferenced by the quality assessment processor 140 may be trained to automatically generate an objective image quality metric based on analysis of image loops of ultrasound images using database(s) 220 of classified ultrasound images and/or image loops of anatomical structures.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 6:
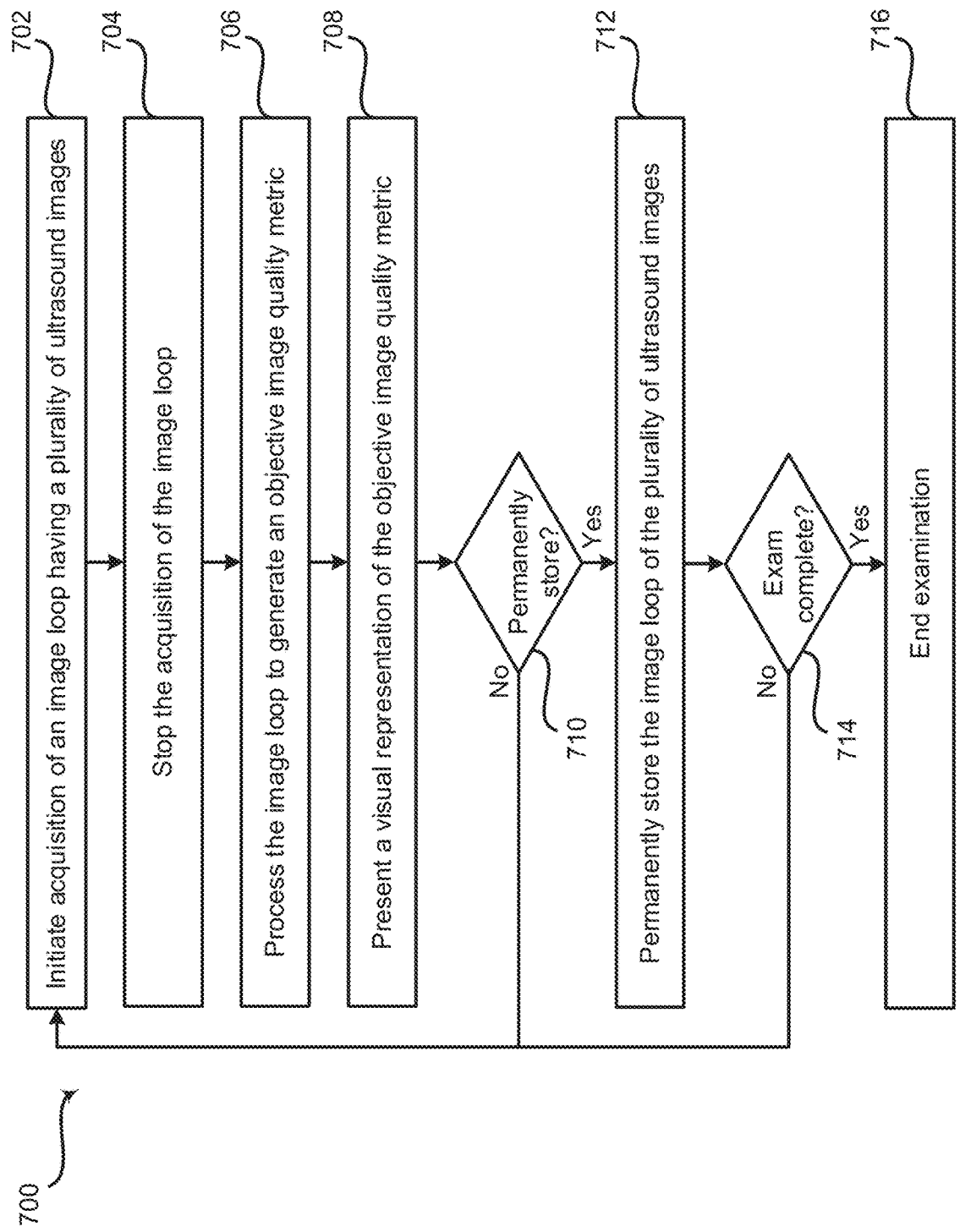
FIG. 6 is a flow chart illustrating exemplary steps that may be utilized for providing an objective image quality metric of an image loop of ultrasound images after acquisition of the image loop and prior to permanently storing the image loop, in accordance with various embodiments.

FIG. 6 is a flow chart 700 illustrating exemplary steps 702-716 that may be utilized for providing an objective image quality metric 310, 410, 510, 610 of an image loop of ultrasound images 304, 504 after acquisition of the image loop and prior to permanently storing the image loop, in accordance with various embodiments. Referring to FIG. 6, there is shown a flow chart 700 comprising exemplary steps 702 through 716. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 702, an ultrasound system 100 initiates acquisition of an image loop having a plurality of ultrasound images 304, 504. For example, the ultrasound system 100 may acquire images with an ultrasound probe 104 positioned at a scan position over region of interest. An ultrasound operator may acquire an image loop of a predetermined time period, number of image frames, heart cycle(s), or the like prior to providing a user input, via a user input device 130, such as an image store user input (i.e., retrospective acquisition). Additionally and/or alternatively, the ultrasound operator may acquire an image loop of a predetermined time period, number of image frames, heart cycle(s), or the like after providing a user input, via a user input device 130, such as an image store user input (i.e., prospective acquisition).

At step 704, the ultrasound system 100 stops the acquisition of the image loop. For example, in a retrospective acquisition, the ultrasound probe 104 of the ultrasound system 100 may stop acquiring ultrasound images 304, 504 of the image loop in response to a user input via the user input device 130, such as a selection of an image store button or any suitable user input device 130. Additionally and/or alternatively, in a prospective acquisition, the ultrasound probe 104 of the ultrasound system 100 may stop acquiring ultrasound images 304, 504 of the image loop automatically after a predetermined time period, number of image frames, heart cycle(s), or the like after providing a user input via the user input device 130, such as a selection of an image store button or any suitable user input device 130.

At step 706, a signal processor 132 of the ultrasound system 100 may process the image loop to generate an objective image quality metric 310, 410, 510, 610. For example, a quality assessment processor 140 of the signal processor 132 may receive the image loop of ultrasound images 304, 504 acquired by probe 104. The quality assessment processor 140 may include image analysis algorithms, one or more deep neural networks (e.g., a convolutional neural network) and/or may utilize any suitable form of image analysis techniques or machine learning processing functionality configured to analyze the acquired image loop to automatically generate an objective image quality metric 310, 410, 510, 610 providing feedback identifying problems in the image loop preventing subsequent analysis and measurements of anatomical structure(s) depicted in the image loop of ultrasound images 304, 504. As an example, the quality assessment processor 140 may perform view recognition, structure recognition, spectrum recognition, end diastole estimation, automated functional imaging (AFI) analysis (e.g., trackability of segments), ejection fraction analysis (e.g., end diastole and end systole contour overlap), artificial intelligence (AI) confidence analysis, sphericity analysis, segmentation, automated measurements (e.g., left ventricle (LV) study, apex movement, cardiac automated Doppler, etc.), heart rate compatibility analysis, automated clinical findings (e.g., diastology assessment), image coherence, image tilt/rotation offset, and the like. The quality assessment processor 140 may be configured to identify unsuitable image loops of ultrasound images 304, 504, such as, non-standard images (e.g., not automatically recognized), images that cannot be automatically measured, a varying heartbeat of an image loop in comparison with at least one other image loop, images having inconsistent structural dimensions, foreshortening, non-trackable segments, and/or any suitable image problem. The quality assessment processor 140 may be configured to generate an objective image quality metric 310, 410, 510, 610 based on the analysis of the image loop of ultrasound images 304, 504.

At step 708, the signal processor 132 of the ultrasound system 100 may present a visual representation of the objective image quality metric 310, 410, 510, 610. For example, the quality assessment processor 140 of the signal processor 132 may cause a display system 134 of the ultrasound system 100 to present a visual representation of the objective image quality metric 310, 410, 510, 610 generated at step 706. The objective image quality metric 310, 410, 510, 610 may comprise a graphical representation 310, 510 identifying a problem with the image loop of the plurality of ultrasound images 304, 504, a textual representation 410, 610 identifying the problem with the image loop of the plurality of ultrasound images 304, 504, and/or instructions 410 guiding a user to address the problem with the image loop of the plurality of ultrasound images 304, 504. The objective image quality metric 310, 410, 510, 610 may further include numerical values, grades, symbols, color-coding, directional indicators, and/or the like for identifying problems in the ultrasound image data and/or providing instructions for addressing identified problems in the ultrasound image data. In various embodiments, the objective image quality metric 310, 410, 510, 610 may be presented at the display system 134 with a preview of the image loop of ultrasound images 304, 504 for ultrasound operator review.

At step 710, the signal processor 132 of the ultrasound system 100 determines whether the image loop of ultrasound images 304, 504 will be permanently stored in long-term memory or discarded. For example, if the ultrasound operator is satisfied with the image loop of ultrasound images 304, 504 based on the objective image quality metric 310, 410, 510, 610, the ultrasound operator may provide a user input via a user input device 130, such as an image store button, to permanently store the image loop of ultrasound images 304, 504 to archive 138 and/or any suitable long-term data storage medium at step 712. As another example, if the ultrasound operator is not satisfied with the image loop of ultrasound images 304, 504, the ultrasound operator may select a user input device 130, such as a freeze button, to discard the image loop of ultrasound images 304, 504 and return to step 702 to resume acquisition of an additional image loop of ultrasound images with the ultrasound probe 104. In an exemplary embodiment, the quality assessment processor 140 may additionally and/or alternatively be configured to automatically determine whether to store the image loop of ultrasound images 304, 504 permanently (i.e., long-term storage) or discard the image loop of ultrasound images 304, 504 based on comparison of the objective image quality metric 310, 410, 510, 610 to a pre-defined threshold.

At step 712, the signal processor 132 of the ultrasound system 100 permanently stores the image loop of the plurality of ultrasound images 304, 504. For example, in response to receiving an image store user input at step 710 and/or automatically determining that the objective image quality metric 310, 410, 510, 610 exceeds a pre-defined threshold at step 710, the quality assessment processor 140 stores the image loop of ultrasound images 304, 504 at archive 138 and/or any suitable long-term (i.e., permanent) data storage medium.

At step 714, the signal processor 132 of the ultrasound system 100 determines whether the ultrasound examination is complete. For example, the signal processor 132 may receive an operator selection, via user input device 130, to end the ultrasound examination. If the signal processor 132 does not receive a user input selecting the option to end the ultrasound examination, the method may return to step 702 to resume acquisition of an additional loop of ultrasound images 304, 504. If the signal processor 132 receives a user input selecting the option to end the ultrasound examination, the method proceeds to step 716 and the ultrasound examination ends.

At step 716, the ultrasound examination is completed, ending the process 700.

Aspects of the present disclosure provide a method 700 and system 100 for providing an objective image quality metric 310, 410, 510, 610 of an image loop of ultrasound images 304, 504 after acquisition of the image loop and prior to permanently storing the image loop. In accordance with various embodiments, the method 700 may comprise performing 702, by an ultrasound probe 104 of an ultrasound system 100, an acquisition of an image loop of a plurality of ultrasound images 304, 504. The method 700 may comprise stop performing 704 the acquisition by the ultrasound probe 104 of the image loop of the plurality of ultrasound images 304, 504. The method 700 may comprise processing 706, by at least one processor 132, 140 of the ultrasound system 100 after the stop performing 704 the acquisition by the ultrasound probe 104, the image loop of the plurality of ultrasound images 304, 504 to generate an objective image quality metric 310, 410, 510, 610. The method 700 may comprise causing 708, by the at least one processor 132, 140, a display system 134 to present a visual representation of the objective image quality metric 310, 410, 510, 610.

In an exemplary embodiment, the method 700 comprises receiving 704, by the at least one processor 132, 140, a first user input to stop the acquisition. The stop performing 704 the acquisition is in response to receiving the first user input to stop the acquisition. The method 700 comprises receiving 710, 712, by the at least one processor 132, 140, a second user input to permanently store the image loop of the plurality of ultrasound images 304, 504 after the presentation 708 of the visual representation of the objective image quality metric 310, 410, 510, 610. In a representative embodiment, the method 700 comprises receiving 704, by the at least one processor 132, 140, a first user input to stop the acquisition. The stop performing 704 the acquisition is in response to receiving the first user input to stop the acquisition. The method 700 comprises receiving 710, 702, by the at least one processor 132, 140, a second user input to initiate acquisition 702 of an additional loop of an additional plurality of ultrasound images 304, 504 after the presentation 708 of the visual representation of the objective image quality metric 310, 410, 510, 610. The image loop of the plurality of ultrasound images 304, 504 is discarded without permanently storing the image loop of the plurality of ultrasound images 304, 504 in response to the second user input. In various embodiments, the method 700 comprises receiving 702, by the at least one processor 132, 140, a first user input to initiate the performing the acquisition 702. The stop performing 704 the acquisition is executed automatically in response to a pre-defined user configuration.

In certain embodiments, the method 700 comprises automatically determining 710, by the at least one processor 132, 140, that the objective image quality metric 310, 410, 510, 610 is above a quality threshold. The method 700 comprises permanently storing 712, by the at least one processor 132, 140, the image loop of the plurality of ultrasound images 304, 504 automatically in response to the automatically determining 710 that the objective image quality metric 310, 410, 510, 610 is above the quality threshold. In an exemplary embodiment, the visual representation of the objective image quality metric 310, 410, 510, 610 comprises a graphical representation 310, 510 of the objective image quality metric 310, 410, 510, 610 identifying a problem with the image loop of the plurality of ultrasound images 304, 504, a textual representation 410, 610 of the objective image quality metric 310, 410, 510, 610 identifying the problem with the image loop of the plurality of ultrasound images 304, 504, and/or instructions 410 guiding a user to address the problem with the image loop of the plurality of ultrasound images 304, 504. In a representative embodiment, the method 700 comprises causing 708, by the at least one processor 132, 140, the display system 134 to present the image loop of the plurality of ultrasound images 304, 504 with the visual representation of the objective image quality metric 310, 410, 510, 610. In various embodiments, the objective image quality metric 310, 410, 510, 610 comprises a strain analysis metric 510, 610 identifying a trackability 512 of each of a plurality of segments of an anatomical structure depicted in the image loop of the plurality of ultrasound images 304, 504. The trackability 512 of each of the plurality of segments corresponding with an ability to perform a strain analysis. In certain embodiments, the objective image quality metric 310, 410, 510, 610 comprises a foreshortening metric 310, 410 identifying an amount of movement 312, 314 of an apical point depicted in the image loop of the plurality of ultrasound images 304, 504 over a time period. In an exemplary embodiment, the objective image quality metric 310, 410, 510, 610 comprises a heart rate compatibility metric identifying whether a first heart rate corresponding with the image loop of the plurality of ultrasound images 304, 504 is within a compatibility threshold with at least one other heart rate corresponding with at least one other image loop permanently stored at an archive 138 of the ultrasound system 100.

Various embodiments provide a system 100 for providing an objective image quality metric 310, 410, 510, 610 of an image loop of ultrasound images 304, 504 after acquisition of the image loop and prior to permanently storing the image loop. The system 100 may comprise an ultrasound probe 104, at least one processor 132, 140, and a display system 134. The ultrasound probe 104 may be configured to perform an acquisition of an image loop of a plurality of ultrasound images 304, 504. The ultrasound probe 104 may be configured to stop performing the acquisition of the image loop of the plurality of ultrasound images 304, 504. The at least one processor 132, 140 may be configured to process the image loop of the plurality of ultrasound images 304, 504 to generate an objective image quality metric 310, 410, 510, 610 after the acquisition by the ultrasound probe 104 is stopped. The display system 134 may be configured to present a visual representation of the objective image quality metric 310, 410, 510, 610.

In a representative embodiment, the at least one processor 132, 140 is configured to receive a first user input to stop performing the acquisition. The acquisition is stopped in response to receiving the first user input to stop performing the acquisition. The at least one processor 132, 140 is configured to receive a second user input to permanently store the image loop of the plurality of ultrasound images 304, 504 after the presentation of the visual representation of the objective image quality metric 310, 410, 510, 610. In various embodiments, the at least one processor 132, 140 is configured to receive a first user input to stop performing the acquisition. The acquisition is stopped in response to receiving the first user input to stop performing the acquisition. The at least one processor 132, 140 is configured to receive a second user input to initiate acquisition of an additional loop of an additional plurality of ultrasound images after the presentation of the visual representation of the objective image quality metric 310, 410, 510, 610. The image loop of the plurality of ultrasound images 304, 504 is discarded without permanently storing the image loop of the plurality of ultrasound images 304, 504 in response to the second user input. In certain embodiments, the at least one processor 132, 140 is configured to receive a first user input to initiate the ultrasound probe 104 to perform the acquisition. The acquisition by the ultrasound probe 104 is stopped automatically in response to a pre-defined user configuration. In an exemplary embodiment, the at least one processor 132, 140 is configured to automatically determine that the objective image quality metric 310, 410, 510, 610 is above a quality threshold. The at least one processor 132, 140 is configured to permanently store the image loop of the plurality of ultrasound images 304, 504 automatically in response to the automatic determination that the objective image quality metric 310, 410, 510, 610 is above the quality threshold. In a representative embodiment, the visual representation of the objective image quality metric 310, 410, 510, 610 comprises a graphical representation 310, 510 of the objective image quality metric 310, 410, 510, 610 identifying a problem with the image loop of the plurality of ultrasound images 304, 504, a textual representation 410, 610 of the objective image quality metric 310, 410, 510, 610 identifying the problem with the image loop of the plurality of ultrasound images 304, 504, and/or instructions 410 guiding a user to address the problem with the image loop of the plurality of ultrasound images 304, 504.

In various embodiments, the display system 134 is configured to present the image loop of the plurality of ultrasound images 304, 504 with the visual representation of the objective image quality metric 310, 410, 510, 610. In certain embodiments, the objective image quality metric 310, 410, 510, 610 comprises a strain analysis metric 510, 610 identifying a trackability 512 of each of a plurality of segments of an anatomical structure depicted in the image loop of the plurality of ultrasound images 304, 504. The trackability 512 of each of the plurality of segments corresponds with an ability to perform a strain analysis. In an exemplary embodiment, the objective image quality metric 310, 410, 510, 610 comprises a foreshortening metric 310, 410 identifying an amount of movement 312, 314 of an apical point depicted in the image loop of the plurality of ultrasound images 304, 504 over a time period. In a representative embodiment, the objective image quality metric 310, 410, 510, 610 comprises a heart rate compatibility metric identifying whether a first heart rate corresponding with the image loop of the plurality of ultrasound images 304, 504 is within a compatibility threshold with at least one other heart rate corresponding with at least one other image loop permanently stored at an archive 138 of the ultrasound system 100.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing an objective image quality metric of an image loop of ultrasound images after acquisition of the image loop and prior to permanently storing the image loop.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
performing, by an ultrasound probe of an ultrasound system, an acquisition of an image loop of a plurality of ultrasound images;
stop performing the acquisition by the ultrasound probe of the image loop of the plurality of ultrasound images;
automatically processing the image loop of the plurality of ultrasound images, by at least one processor of the ultrasound system after the stop performing the acquisition by the ultrasound probe and prior to permanently storing or discarding the image loop of the plurality of ultrasound images, to generate an objective image quality metric identifying a problem with the image loop of the plurality of ultrasound images that prevents subsequent analysis and/or measurement; and
causing, by the at least one processor, a display system to present a visual representation of the objective image quality metric.

2. The method of claim 1, comprising:
receiving, by the at least one processor, a first user input to stop the acquisition, wherein the stop performing the acquisition is in response to receiving the first user input to stop the acquisition; and
receiving, by the at least one processor, a second user input to permanently store the image loop of the plurality of ultrasound images after the presentation of the visual representation of the objective image quality metric.

3. The method of claim 1, comprising:
receiving, by the at least one processor, a first user input to stop the acquisition, wherein the stop performing the acquisition is in response to receiving the first user input to stop the acquisition; and
receiving, by the at least one processor, a second user input to initiate acquisition of an additional loop of an additional plurality of ultrasound images after the presentation of the visual representation of the objective image quality metric, wherein the image loop of the plurality of ultrasound images is discarded without permanently storing the image loop of the plurality of ultrasound images in response to the second user input.

4. The method of claim 1, comprising receiving, by the at least one processor, a first user input to initiate the performing the acquisition, wherein the stop performing the acquisition is executed automatically in response to a pre-defined user configuration.

5. The method of claim 1, comprising:
automatically determining, by the at least one processor, that the objective image quality metric is above a quality threshold; and
permanently storing, by the at least one processor, the image loop of the plurality of ultrasound images automatically in response to the automatically determining that the objective image quality metric is above the quality threshold.

6. The method of claim 1, wherein the visual representation of the objective image quality metric comprises:
a graphical representation of the objective image quality metric identifying the problem with the image loop of the plurality of ultrasound images,
a textual representation of the objective image quality metric identifying the problem with the image loop of the plurality of ultrasound images, and/or
instructions guiding a user to address the problem with the image loop of the plurality of ultrasound images.

7. The method of claim 1, comprising causing, by the at least one processor, the display system to present the image loop of the plurality of ultrasound images with the visual representation of the objective image quality metric.

8. The method of claim 1, wherein the objective image quality metric comprises a strain analysis metric identifying a trackability of each of a plurality of segments of an anatomical structure depicted in the image loop of the plurality of ultrasound images, the trackability of each of the plurality of segments corresponding with an ability to perform a strain analysis.

9. The method of claim 1, wherein the objective image quality metric comprises a foreshortening metric identifying an amount of movement of an apical point depicted in the image loop of the plurality of ultrasound images over a time period.

10. The method of claim 1, wherein the objective image quality metric comprises a heart rate compatibility metric identifying whether a first heart rate corresponding with the image loop of the plurality of ultrasound images is within a compatibility threshold with at least one other heart rate corresponding with at least one other image loop permanently stored at an archive of the ultrasound system.

11. A system comprising:
an ultrasound probe configured to:
perform an acquisition of an image loop of a plurality of ultrasound images; and
stop performing the acquisition of the image loop of the plurality of ultrasound images;
at least one processor configured to automatically process the image loop of the plurality of ultrasound images, after the acquisition by the ultrasound probe is stopped and prior to permanently storing or discarding the image loop of the plurality of ultrasound images, to generate an objective image quality metric identifying a problem with the image loop of the plurality of ultrasound images that prevents subsequent analysis and/or measurement; and
a display system configured to present a visual representation of the objective image quality metric.

12. The system of claim 11, wherein the at least one processor is configured to:
receive a first user input to stop performing the acquisition, wherein the acquisition is stopped in response to receiving the first user input to stop performing the acquisition; and
receive a second user input to permanently store the image loop of the plurality of ultrasound images after the presentation of the visual representation of the objective image quality metric.

13. The system of claim 11, wherein the at least one processor is configured to:
receive a first user input to stop performing the acquisition, wherein the acquisition is stopped in response to receiving the first user input to stop performing the acquisition; and
receive a second user input to initiate acquisition of an additional loop of an additional plurality of ultrasound images after the presentation of the visual representation of the objective image quality metric, wherein the image loop of the plurality of ultrasound images is discarded without permanently storing the image loop of the plurality of ultrasound images in response to the second user input.

14. The system of claim 11, wherein the at least one processor is configured to receive a first user input to initiate the ultrasound probe to perform the acquisition, wherein the acquisition by the ultrasound probe is stopped automatically in response to a pre-defined user configuration.

15. The system of claim 11, wherein the at least one processor is configured to:
   automatically determine that the objective image quality metric is above a quality threshold; and
   permanently store the image loop of the plurality of ultrasound images automatically in response to the automatic determination that the objective image quality metric is above the quality threshold.

16. The system of claim 11, wherein the visual representation of the objective image quality metric comprises:
   a graphical representation of the objective image quality metric identifying the problem with the image loop of the plurality of ultrasound images,
   a textual representation of the objective image quality metric identifying the problem with the image loop of the plurality of ultrasound images, and/or
   instructions guiding a user to address the problem with the image loop of the plurality of ultrasound images.

17. The system of claim 11, wherein the display system is configured to present the image loop of the plurality of ultrasound images with the visual representation of the objective image quality metric.

18. The system of claim 11, wherein the objective image quality metric comprises a strain analysis metric identifying a trackability of each of a plurality of segments of an anatomical structure depicted in the image loop of the plurality of ultrasound images, the trackability of each of the plurality of segments corresponding with an ability to perform a strain analysis.

19. The system of claim 11, wherein the objective image quality metric comprises a foreshortening metric identifying an amount of movement of an apical point depicted in the image loop of the plurality of ultrasound images over a time period.

20. The system of claim 11, wherein the objective image quality metric comprises a heart rate compatibility metric identifying whether a first heart rate corresponding with the image loop of the plurality of ultrasound images is within a compatibility threshold with at least one other heart rate corresponding with at least one other image loop permanently stored at an archive of the ultrasound system.

* * * * *